US006937697B2

(12) United States Patent
Nishide et al.

(10) Patent No.: US 6,937,697 B2
(45) Date of Patent: Aug. 30, 2005

(54) X-RAY DATA COLLECTING APPARATUS AND X-RAY CT APPARATUS

(75) Inventors: Akihiko Nishide, Tokyo (JP); Hirofumi Yanagita, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 58 days.

(21) Appl. No.: 10/738,053

(22) Filed: Dec. 17, 2003

(65) Prior Publication Data

US 2004/0131144 A1 Jul. 8, 2004

(30) Foreign Application Priority Data

Dec. 27, 2002 (JP) ........................................ 2002-380943

(51) Int. Cl.[7] ................................................. H05G 1/44
(52) U.S. Cl. ..................................................... 378/108
(58) Field of Search ............................... 378/4, 19, 97, 378/108, 207, 901

(56) References Cited

U.S. PATENT DOCUMENTS

| 5,341,460 A | 8/1994 | Tam ............................ 345/419 |
| 6,263,008 B1 | 7/2001 | Lai .............................. 378/19 |
| 6,322,248 B1 | 11/2001 | Yanagita et al. ............. 378/205 |

*Primary Examiner*—David V. Bruce
*Assistant Examiner*—Courtney Thomas
(74) *Attorney, Agent, or Firm*—Carl B. Horton, Esq.; Armstrong Teasdale LLP

(57) ABSTRACT

An X-ray data collecting apparatus includes a first integrating means periodically executes sequential integration on detected signals from a plurality of X-ray detector elements corresponding to measurement channels in an X-ray detection apparatus at a constant time difference over a constant time period longer than the time difference; a second integrating means periodically executes sequential integration on detected signals from a plurality of X-ray detector elements corresponding to reference channels in the plurality of detector element rows in the X-ray detection apparatus at the same time difference as the constant time difference over the same time period as the constant time period; and a correcting means X-ray-dose corrects signals integrated by the first integrating means by signals integrated by the second integrating means that are integrated at the same time as the signals integrated by the first integration means, respectively.

16 Claims, 13 Drawing Sheets

24 (ik)

240

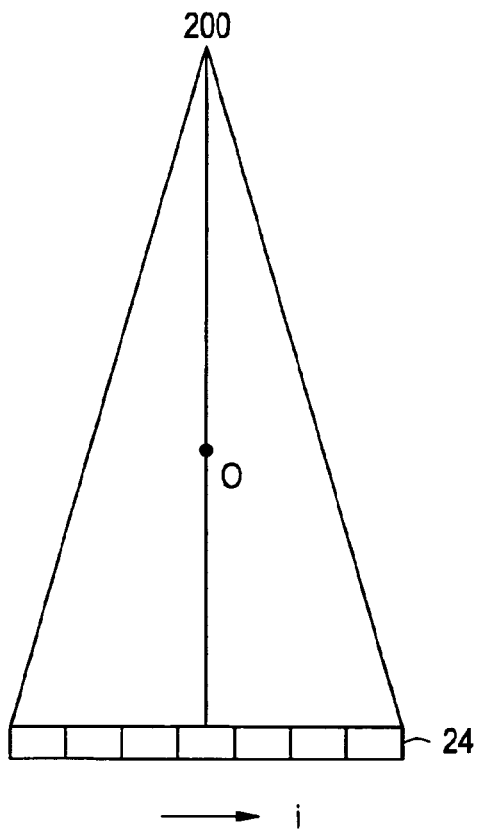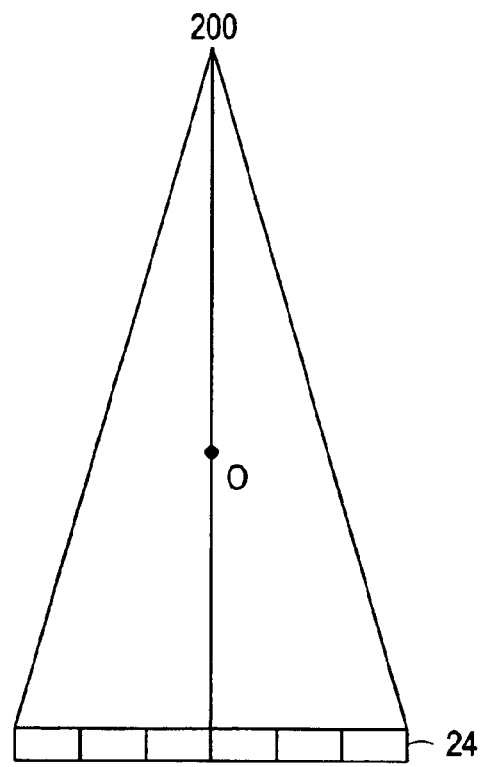

X-RAY DATA COLLECTING APPARATUS AND X-RAY CT APPARATUS

CROSS REFERENCE TO RELATED APPLICATIONS

This application claims the benefit of Japanese Application No. 2002-380943 filed Dec. 27, 2002.

BACKGROUND OF THE INVENTION

The present invention relates to an X-ray data collecting apparatus and X-ray CT (computed tomography) apparatus, and more particularly to an apparatus for acquiring X-ray signals using an X-ray detector having a plurality of X-ray detector element rows, and an X-ray CT apparatus comprising such an X-ray data collecting apparatus.

At least one conventional X-ray CT apparatus is known that simultaneously acquires X-ray signals for a plurality of slices using an X-ray detector having a plurality of X-ray detector element rows arranged in parallel, and produces an image based on such X-ray signals. (For example, see Patent Document 1).

Moreover, at least one conventional technique for obtaining X-ray signals representing parallel beam X-rays from fan beam X-rays is known that involves adjusting signal collection times on an X-ray detector channel-by-channel basis. (For example, see Patent Document 2).

Furthermore, the X-ray signals are collected as integral values over a constant time period, and at least one conventional technique for obtaining reference X-ray signals adapted to varying collection times for different X-ray detector channels is known that involves repeating integration and resetting of the reference X-ray signals at subdivided times of the collection times, and summing the resulting plurality of integral signals over respective integral time periods for the channels. (For example, see Patent Document 3).

[Patent Document 1]

Japanese Patent Application Laid Open No. 2001-327386 (Pages 2–9, FIGS. 1–9).

[Patent Document 2]

Japanese Patent Application Publication No. H6-83709 (Pages 1–6, FIGS. 1–10).

[Patent Document 3]

Japanese Patent Application Publication No. H4-78258 (Pages 1–5, FIGS. 1–3).

By combining these conventional techniques, it is possible to construct an X-ray CT apparatus for collecting X-ray signals representing parallel beam X-rays from fan beam X-rays using an X-ray detector having a plurality of X-ray detector element rows, correcting the signals by reference X-ray signals, and producing an image based on the corrected signals.

Such a technique, however, obtains the reference X-ray signals at the collection times by summing signals obtained by repeating integration/resetting at subdivided times, and thus, the effective integration time for the reference X-ray signals is shorter than the integration time for measured X-ray signals, resulting in a corresponding decline of S/N (signal-to-noise ratio) of the signals.

SUMMARY OF THE INVENTION

It is therefore an object of the present invention to provide an X-ray data collecting apparatus for collecting X-ray signals representing parallel beam X-rays from fan beam X-rays using an X-ray detector having a plurality of X-ray detector element rows, and correcting the signals by reference X-ray signals, which apparatus offers good S/N of the signals, and an X-ray CT apparatus comprising such an X-ray data collecting apparatus.

(1) The present invention in one aspect for solving the aforementioned problems is an X-ray data collecting apparatus characterized in comprising: X-ray emitting/detecting means having an X-ray emitting apparatus including an X-ray tube for emitting a fan-shaped X-ray beam and an X-ray detection apparatus including a plurality of detector element rows in a thickness direction of said fan-shaped X-ray beam, in each of which rows a plurality of X-ray detector elements are arranged in an extent direction of said fan-shaped X-ray beam, said X-ray detection apparatus disposed to face said X-ray emitting apparatus interposing a subject, said X-ray emitting/detecting means rotating around said subject; first integrating means for periodically executing sequential integration on detected signals from a plurality of X-ray detector elements corresponding to measurement channels in said X-ray detection apparatus at a constant time difference over a constant time period longer than said time difference; second integrating means for periodically executing sequential integration on detected signals from a plurality of X-ray detector elements corresponding to reference channels in said plurality of detector element rows in said X-ray detection apparatus at the same time difference as said constant time difference over the same time period as said constant time period; and correcting means for X-ray-dose correcting signals integrated by said first integrating means by signals integrated by said second integrating means that are integrated at the same time as the signals integrated by said first integration means, respectively.

In the invention of this aspect, the first integrating means periodically executes sequential integration on detected signals from a plurality of X-ray detector elements corresponding to measurement channels in the X-ray detection apparatus at a constant time difference over a constant time period longer than the time difference; the second integrating means periodically executes sequential integration on detected signals from a plurality of X-ray detector elements corresponding to reference channels in the plurality of detector element rows in the X-ray detection apparatus at the same time difference as the constant time difference over the same time period as the constant time period; and the correcting means corrects signals integrated by the first integrating means by signals integrated by the second integrating means that are integrated at the same time as the signals integrated by the first integration means, and therefore, the integration time for the reference X-ray signals is the same as that for the measured X-ray signals, resulting in good S/N of the signals.

(2) The present invention in another aspect for solving the aforementioned problems is an X-ray CT apparatus characterized in comprising: X-ray emitting/detecting means having an X-ray emitting apparatus including an X-ray tube for emitting a fan-shaped X-ray beam and an X-ray detection apparatus including a plurality of detector element rows in a thickness direction of said fan-shaped X-ray beam, in each of which rows a plurality of X-ray detector elements are arranged in an extent direction of said fan-shaped X-ray beam, said X-ray detection apparatus disposed to said X-ray face emitting apparatus interposing a subject, said X-ray emitting/detecting means rotating around said subject; first integrating means for periodically executing sequential integration on detected signals from a plurality of X-ray detector elements corresponding to measurement channels in said X-ray detection apparatus at a constant time difference over a constant time period longer than said time difference; second integrating means for periodically executing sequential integration on detected signals from a plurality of X-ray detector elements corresponding to reference channels in said plurality of detector element rows in said X-ray detection apparatus at the same time difference as said constant time difference over the same time period as said constant time period; correcting means for X-ray-dose correcting signals integrated by said first integrating means by signals integrated by said second integrating means that are integrated at the same time as the signals integrated by said first integration means, respectively; and image reconstructing means for producing an image based on said corrected signals.

In the invention of this aspect, the first integrating means periodically executes sequential integration on detected signals from a plurality of X-ray detector elements corresponding to measurement channels in the X-ray detection apparatus at a constant time difference over a constant time period longer than the time difference; the second integrating means periodically executes sequential integration on detected signals from a plurality of X-ray detector elements corresponding to reference channels in the plurality of detector element rows in the X-ray detection apparatus at the same time difference as the constant time difference over the same time period as the constant time period; and the correcting means corrects signals integrated by the first integrating means by signals integrated by the second integrating means that are integrated at the same time as the signals integrated by the first integration means, and therefore, the integration time for the reference X-ray signals is the same as that for the measured X-ray signals, resulting in good S/N of the signals. Moreover, an image produced based on such signals is improved in quality.

Preferably, based on the sampling theorem, said X-ray detection apparatus is quarter-offset with respect to said X-ray emitting apparatus, so that X-ray signals having an X-ray path different by ½ of the measurement channel pitch may be obtained as opposite view data.

Preferably, said plurality of X-ray detector elements are arranged symmetrically with respect to a center of the detector element rows, so that X-ray signals having the same X-ray path may be obtained as opposite view data.

Preferably, said time difference is one such that X-ray beams impinging upon a plurality of measurement channels are parallel, so that X-ray signals representing parallel beam X-rays can be collected from fan beam X-rays.

Preferably, when a difference in time of integration between adjacent channels in said detector element row is represented as $\Delta\theta/\Delta\phi$ (normalized by $\Delta\phi$), the number of channels handled per unit by processing means for sequentially processing output signals from at least one of said first integrating means and said second integrating means is represented by n, and an integer having no divisor in common with n is represented as p, said time difference enables these variables to satisfy:

$$\frac{\Delta\theta}{\Delta\phi} = \frac{p}{n},$$

where:
$\Delta\theta$: an angular step difference for measurement channels, and $\Delta\phi$: an angular step difference for views, so that signals for n channels may be sequentially processed without overlap.

Preferably, said apparatus further comprises normalizing means for normalizing output signals from said second integrating means, so that influence from the X-ray intensity distribution in the side-by-side arrangement direction of the detector element rows can be corrected.

Preferably, said normalizing means determines a plurality of integral values beforehand by integrating detected signals from all reference channels at the same time over said constant time period, and normalizes said output signals from said second integrating means for the reference channels by said plurality of integral values of the same reference channels, respectively, so that the normalization may be suitably achieved.

Preferably, if $$1 - \varepsilon \leq \left|\frac{R_{k(view)}}{R_{k(view-1)}}\right| \leq 1 + \varepsilon,$$

where:
$R_k(view)$: an integral value of signals of a current view at a reference channel k over said constant time period,
$R_k(view-1)$: an integral value of signals of a previous view at a reference channel k over said constant time period, and
$\varepsilon$: an allowance, does not hold, said correcting means conducts the correction using, in place of $R_k(view)$, $$R'_{k(view)} = R_{k(view-1)} \cdot \frac{mA_{(view)}}{mA_{(view-1)}},$$

where:
$mA(view)$: a tube current of the X-ray tube for the current view, and
$mA(view-1)$: a tube current of the X-ray tube for the previous view, so that influence from a temporary fault in the reference X-ray signals can be reduced.

Therefore, the present invention provides an X-ray data collecting apparatus for collecting X-ray signals representing parallel beam X-rays from fan beam X-rays using an X-ray detector having a plurality of X-ray detector element rows, and correcting the signals by reference X-ray signals, which apparatus offers good S/N of the signals, and an X-ray CT apparatus comprising such an X-ray data collecting apparatus.

Further objects and advantages of the present invention will be apparent from the following description of the preferred embodiments of the invention as illustrated in the accompanying drawings.

BRIEF DESCRIPTION OF THE DRAWINGS

FIG. 8 shows a geometrical relationship between the X-ray focal spot and X-ray detector.

FIG. 9 shows a geometrical relationship between the X-ray focal spot and X-ray detector.

DETAILED DESCRIPTION OF THE INVENTION

Figure 1:
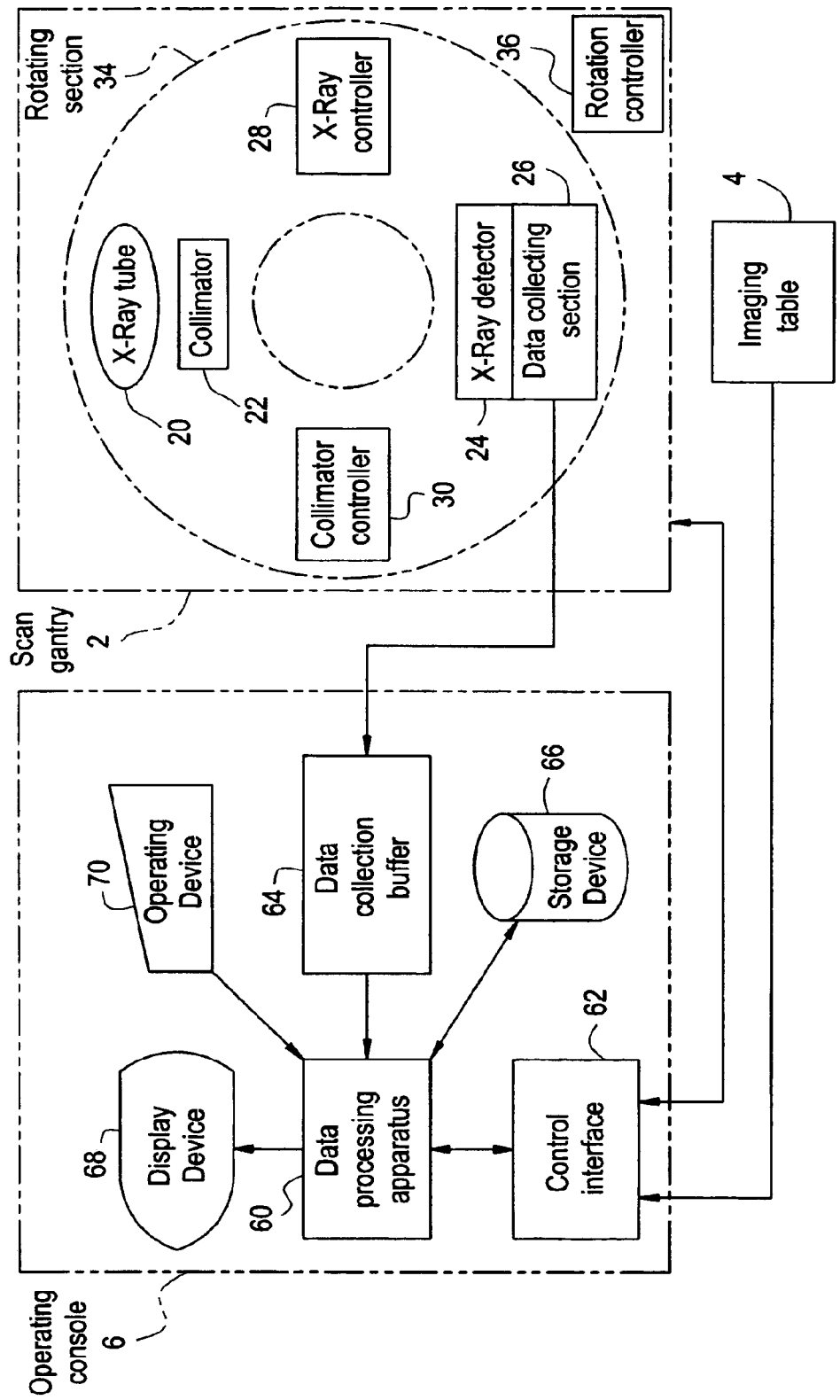
FIG. 1 is a block diagram of an apparatus in accordance with an embodiment of the present invention.

Several embodiments of the present invention will now be described in detail with reference to the accompanying drawings. FIG. 1 shows a block diagram of an X-ray CT apparatus, which is an embodiment of the present invention. The configuration of the apparatus represents an embodiment of the apparatus in accordance with the present invention.

As shown in FIG. 1, the apparatus comprises a scan gantry 2, an imaging table 4 and an operating console 6. The scan gantry 2 has an X-ray tube 20. X-rays (not shown) emitted from the X-ray tube 20 are formed into a fan-shaped X-ray beam by a collimator 22, and projected toward a multi-row X-ray detector 24. The fan-shaped X-ray beam is sometimes referred to as fan beam X-rays. A portion comprised of the X-ray tube 20 and collimator 22 is an embodiment of the X-ray emitting apparatus in the present invention.

The X-ray detector 24 has a plurality of rows of detector elements arranged in a two-dimensional array. The X-ray detector 24 is an embodiment of the X-ray detection apparatus in the present invention. The configuration of the X-ray detector 24 will be described in detail later. The X-ray tube 20, collimator 22 and X-ray detector 24 together constitute an X-ray emitting/detecting apparatus. The X-ray emitting/detecting apparatus is an embodiment of the X-ray emitting/detecting means in the present invention. The X-ray emitting/detecting apparatus will be described in detail later.

The X-ray detector 24 is connected with a data collecting section 26. The data collecting section 26 collects signals detected by the individual detector elements in the X-ray detector 24 as digital data.

The X-ray tube 20 is controlled by an X-ray controller 28. The X-ray controller 28 controls the tube voltage and tube current of the X-ray tube 20. The interconnection between the X-ray tube 20 and X-ray controller 28 is omitted in the drawing. The collimator 22 is controlled by a collimator controller 30. The interconnection between the collimator 22 and collimator controller 30 is omitted in the drawing.

The above-described components from the X-ray tube 20 through the collimator controller 30 are mounted on a rotating section 34 of the scan gantry 2. The rotation of the rotating section 34 is controlled by a rotation controller 36. The interconnection between the rotating section 34 and rotation controller 36 is omitted in the drawing.

The imaging table 4 is configured to carry a subject to be imaged (not shown) into and out of an X-ray irradiation space in the scan gantry 2. The relationship between the subject and X-ray irradiation space will be described in detail later.

The operating console 6 has a data processing apparatus 60. The data processing apparatus 60 is comprised of, for example, a computer. The data processing apparatus 60 is connected with a control interface 62. The control interface 62 is connected with the scan gantry 2 and the imaging table 4. The data processing apparatus 60 controls the scan gantry 2 and imaging table 4 via the control interface 62.

The data collecting section 26, X-ray controller 28, collimator controller 30 and rotation controller 36 in the scan gantry 2 are controlled via the control interface 62. The individual connections between these sections and the control interface 62 are omitted in the drawing.

The data processing apparatus 60 is also connected with a data collection buffer 64. The data collection buffer 64 is connected with the data collecting section 26 in the scan gantry 2. Transmitted X-ray data collected at the data collecting section 26 are input to the data processing apparatus 60 via the data collection buffer 64. A measured value of the tube current of the X-ray tube 20 is also input to the data processing apparatus 60 via the data collection buffer 64.

The data processing apparatus 60 performs image reconstruction using the transmitted X-ray data for a plurality of views collected via the data collection buffer 64. The image reconstruction is performed using a filtered backprojection technique, for example. The data processing apparatus 60 is an embodiment of the image reconstructing means in the present invention.

The data processing apparatus 60 is also connected with a storage device 66. The storage device 66 stores several kinds of data, programs, and so forth. Several kinds of data processing relating to imaging are achieved by the data processing apparatus 60 executing the programs stored in the storage device 66.

The data processing apparatus 60 is further connected with a display device 68 and an operating device 70. The display device 68 displays the reconstructed image and other information output from the data processing apparatus 60. The operating device 70 is operated by a user, and supplies several kinds of instructions and information to the data processing apparatus 60. The user interactively operates the present apparatus using the display device 68 and operating device 70.

Figure 2:
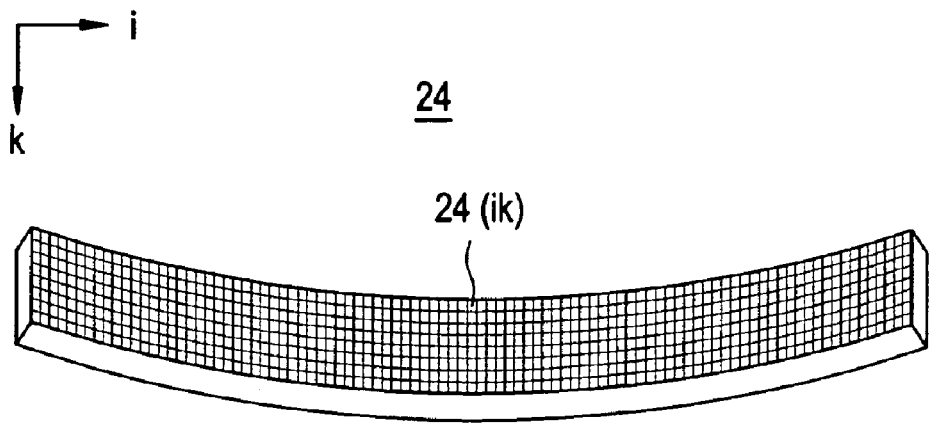
FIG. 2 shows a configuration of an X-ray detector.

FIG. 2 schematically shows a configuration of the X-ray detector 24. As shown, the X-ray detector 24 is a multi-channel X-ray detector having a plurality of X-ray detector elements 24(ik) arranged in a two-dimensional array. The plurality of X-ray detector elements 24(ik) together form an X-ray impingement surface curved as a cylindrical concavity.

Reference symbol i represents a channel index and, for example, i=−500, −499, . . . , −1, 0, 1, . . . , 499. Reference symbol k represents a row index, and, for example, k=0, 1, 2, . . . , 15. The detector elements 24(ik) that have the same row index k together constitute a detector element row. The X-ray detector 24 is not limited to having sixteen detector element rows, and may have any appropriate plural number of rows.

Figure 3:
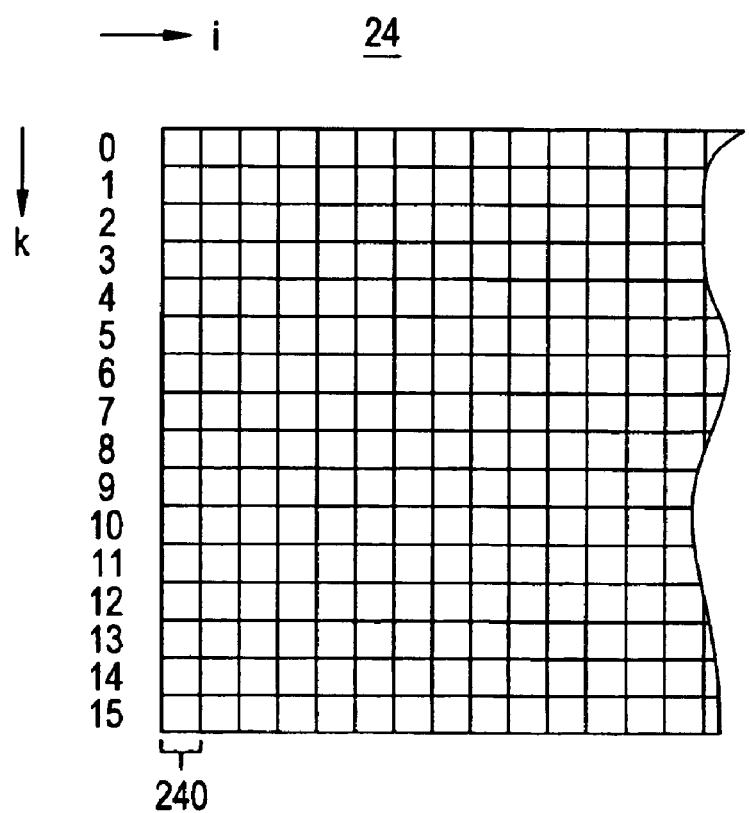
FIG. 3 shows part of the configuration of the X-ray detector.

The first X-ray detector element in each row is a reference channel 240, as shown in FIG. 3. The reference channels 240 are used for measuring reference X-ray signals for X-ray intensity correction. The reference channels 240 are not limited to lying at the first in the rows but may lie at appropriate positions in one or both of edges of the X-ray detector 24. All channels other than the reference channels are measurement channels.

Each X-ray detector element 24(*ik*) is formed of a combination of a scintillator and a photodiode, for example. However, it should be noted that the X-ray detector element 24(*ik*) is not limited to such but may be a semiconductor X-ray detector element using cadmium telluride (CdTe) or the like, or an ionization chamber X-ray detector element using xenon (Xe) gas, for example.

Figure 4A:
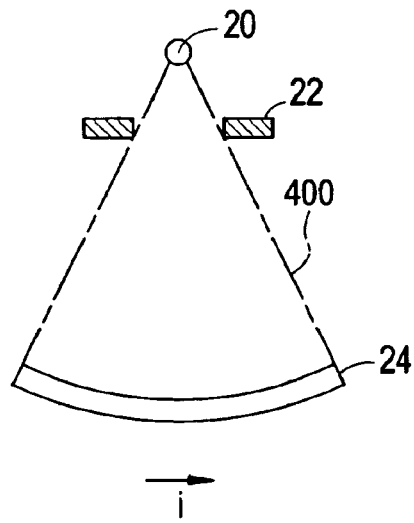
FIG. 4 shows a configuration of an X-ray emitting/detecting apparatus.
Figure 4B:
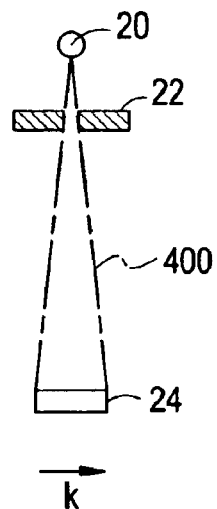

FIG. 4 shows the interrelationship among the X-ray tube 20, collimator 22 and X-ray detector 24 in the X-ray emitting/detecting apparatus. FIG. 4(1) is a view from the front of the scan gantry 2 and (2) is a view from the side thereof. As shown, the X-rays emitted from the X-ray tube 20 are formed into a fan-shaped X-rays by the collimator 22, and projected toward the X-ray detector 24.

FIG. 4(1) illustrates the extent of the fan beam X-rays 400 in the i-direction. The i-direction is the channel arrangement direction in each detector element row in the X-ray detector 24. The extent in the i-direction will be sometimes referred to simply as the extent. FIG. 4(2) illustrates the extent of the fan beam X-rays 400 in the k-direction. The k-direction is a side-by-side arrangement direction for the detector element rows in the X-ray detector 24. The extent in the k-direction will be sometimes referred to simply as the thickness.

Figure 5:
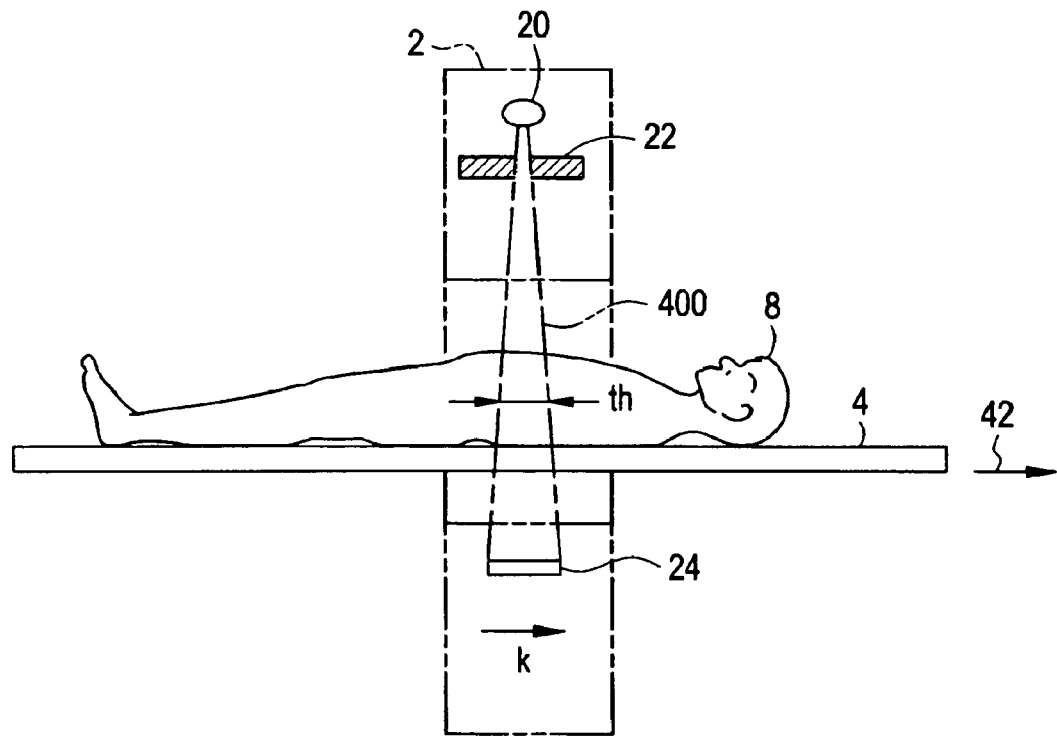
FIG. 5 shows a relationship between the X-ray emitting/detecting apparatus and a subject.

A subject 8 placed on the imaging table 4 is carried into the X-ray irradiation space with the subject's body axis intersecting the fan beam X-rays 400, as exemplarily shown in FIG. 5. The scan gantry 2 has a cylindrical structure containing therein the X-ray emitting/detecting apparatus.

The X-ray irradiation space is formed in the internal space of the cylindrical structure of the scan gantry 2. An image of the subject 8 sliced by the fan beam X-rays 400 is projected onto the X-ray detector 24. The X-rays passing through the subject 8 are detected by the X-ray detector 24. The thickness th of the fan beam X-rays 400 impinging upon the subject 8 is regulated by the degree of opening of an aperture of the collimator 22.

The X-ray emitting/detecting apparatus comprised of the X-ray tube 20, collimator 22 and X-ray detector 24 continuously rotates (or scans) around the body axis of the subject 8 while maintaining their interrelationship. Thus, an axial scan is conducted.

When the imaging table 4 is continuously moved in the body axis direction of the subject 8 as indicated by an arrow 42 simultaneously with the rotation of the X-ray emitting/detecting apparatus, the X-ray emitting/detecting apparatus will rotate relative to the subject 8 along a helical trajectory surrounding the subject 8. Thus, a scan generally referred to as a helical scan is conducted.

Figure 6:
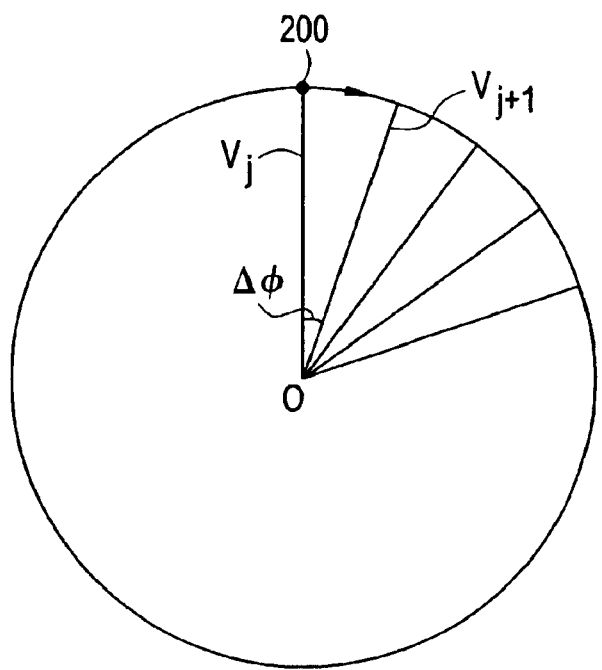
FIG. 6 shows a rotation trajectory of an X-ray focal spot.

Transmitted X-ray data for a plurality of (for example, ca. 1,000) views are collected per rotation of the X-ray emitting/detecting apparatus. A reference position for the plurality of views is defined on a rotation trajectory of an X-ray focal spot 200, as shown in FIG. 6. The angular step difference between views is $\Delta\phi$.

The collection of the transmitted X-ray data is conducted for the plurality of detector element rows in the X-ray detector 24. The collection of the transmitted X-ray data is conducted by the X-ray detector 24, data collecting section 26 and data collection buffer 64 in series.

Figure 7:
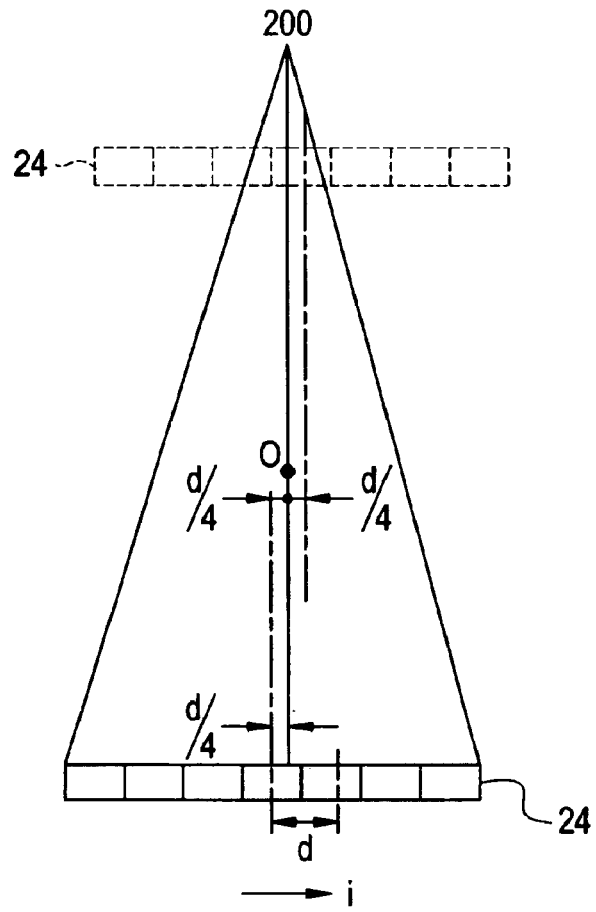
FIG. 7 shows a geometrical relationship between the X-ray focal spot and X-ray detector.

FIG. 7 schematically shows the geometrical relationship between the X-ray tube 20 and X-ray detector 24. As shown, the X-ray detector 24 lies in a relationship such that its center (the center of the center channel) is offset by a distance of ¼ channel pitch d in the i-direction with respect to an extension line of a straight line connecting the X-ray focal spot 200 and center of rotation ○. Such a geometrical relationship is sometimes referred to as a quarter offset.

By such a configuration, X-rays impinging upon the center channel passes through a position offset by d/4 from the center of rotation ○. After the X-ray emitting/detecting apparatus has rotated 180 degrees (dashed line) from that condition, X-rays impinging upon the center channel pass through a position offset by d/4 from the center of rotation ○ in an opposite direction. The same applies to the other channels.

Thus, by interleaving data pairs each having the rotation angle of the X-ray emitting/detecting apparatus different by 180 degrees, i.e., opposite view data pairs, X-ray signals equivalent to those when the channel pitch of the X-ray detector 24 is halved can be obtained. This contributes to improvement of the spatial resolution of a reconstructed image.

If the channel pitch is sufficiently small, the X-ray detector 24 need not be configured with a quarter offset. The geometrical relationship without the quarter offset is shown in FIGS. 8 and 9. In FIG. 8, the center of the center channel lies on an extension line of a straight line connecting the X-ray focal spot 200 and center of rotation ○. In FIG. 9, the border between the center channel and adjacent channel lies on an extension line of a straight line connecting the X-ray focal spot 200 and center of rotation ○. These configurations provide an X-ray detector in which channels are disposed in a horizontally symmetrical manner. By such configurations, X-ray signals having the same X-ray path can be obtained as an opposite view data pair.

Figure 10:
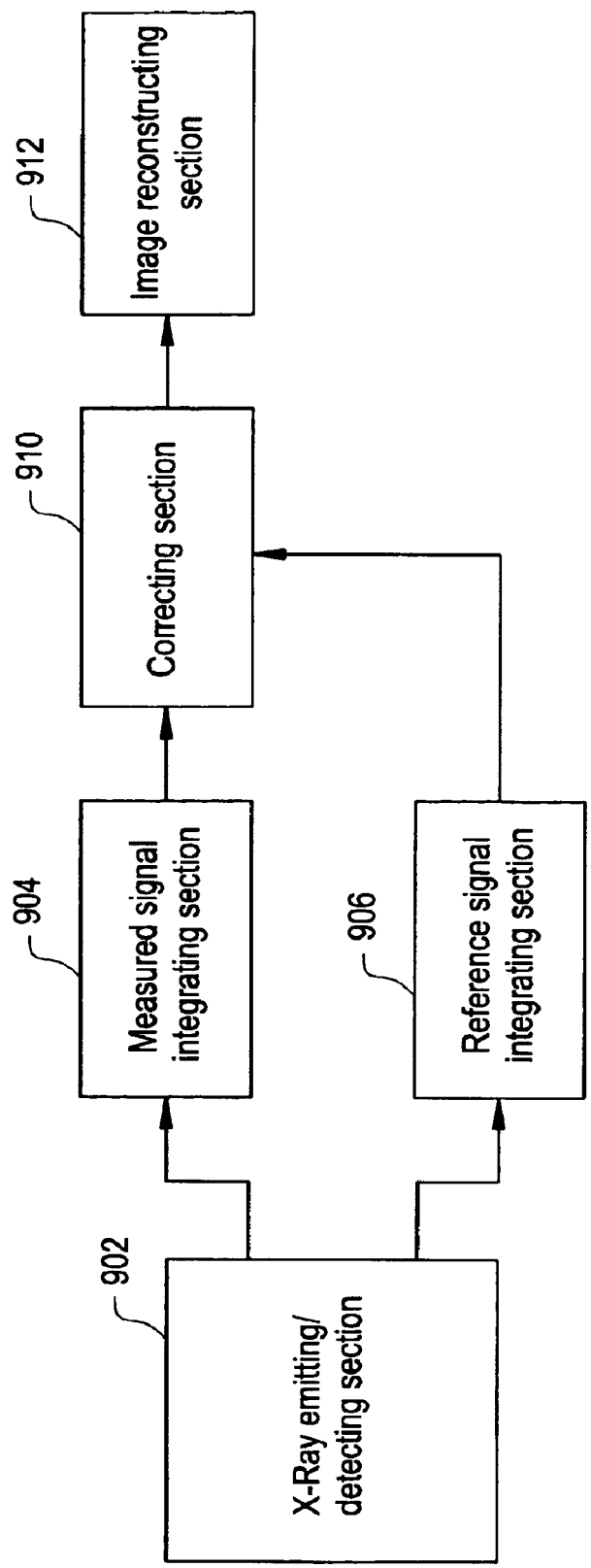
FIG. 10 is a functional block diagram of an apparatus in accordance with an embodiment of the present invention.

FIG. 10 shows a functional block diagram of the present apparatus. As shown, the apparatus is comprised of an X-ray emitting/detecting section 902, a measured signal integrating section 904, a reference signal integrating section 906, a correcting section 910 and an image reconstructing section 912. The components from the X-ray emitting/detecting section 902 through the correcting section 910 constitute an X-ray data collecting apparatus.

The X-ray emitting/detecting section 902 corresponds to the function of the scan gantry 2 shown in FIG. 1 removed of the data collecting section 26. The X-ray emitting/detecting section 902 is an embodiment of the X-ray emitting/detecting means in the present invention.

The measured signal integrating section 904 and reference signal integrating section 906 correspond to a function of the data collecting section 26 shown in FIG. 1. The measured signal integrating section 904 is an embodiment of the first integrating means in the present invention. The reference signal integrating section 906 is an embodiment of the second integrating means in the present invention.

The correcting section 910 corresponds to the function of the data processing apparatus 60 shown in FIG. 1. The correcting section 910 is an embodiment of the correcting means in the present invention. The image reconstructing section 912 corresponds to a function of the data processing apparatus 60 shown in FIG. 1. The image reconstructing section 912 is an embodiment of the image reconstructing means in the present invention.

X-ray signals detected by the X-ray emitting/detecting section 902 are integrated at the measured signal integrating section 904 and reference signal integrating section 906. The measured signal integrating section 904 integrates X-ray detected signals from the measurement channels in the X-ray detector 24. The reference signal integrating section 906 integrates X-ray detected signals from the reference channels 240 in the X-ray detector 24. The integrations by these integrating sections are conducted on a channel-by-channel basis. Signals from the individual channels are integrated at respective predetermined times.

The times of the integration for the signals from the measurement channels are set so that X-ray signals representing parallel beam X-rays are obtained. The parallel beam X-rays represent those X-rays that are parallel in impinging upon the measurement channels. Determination of X-ray signals representing the parallel beam X-rays from the fan beam X-rays is sometimes referred to as fan-parallel transformation.

Figure 11:
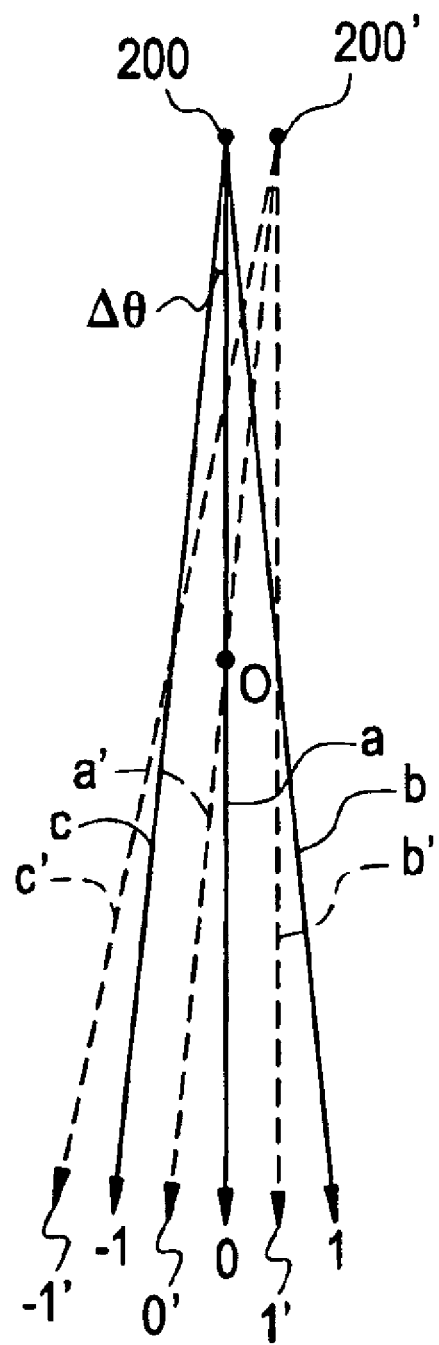
FIG. 11 shows transformation of fan beam data into parallel beam data.

The principle of the fan-parallel transformation will be now explained with reference to FIG. 11. Solid lines in FIG. 11 represent a condition in which three X-rays a, b and c in fan beam X-rays emanating from the X-ray focal spot 200 impinge upon the center channel 0 and adjacent channels 1 and −1 in the X-ray detector 24, respectively. The X-ray a passes through the center of rotation ◯. Representing the channel pitch with respect to the X-ray focal spot 200 as an angle $\Delta\theta$, the angular step difference between the X-rays a, b and c is $\Delta\theta$.

As the X-ray emitting/detecting apparatus rotates, the X-ray focal spot 200 moves to a position designated by reference numeral 200', and at that time, the center channel and adjacent channels lie at positions indicated by reference numerals 0', 1' and −1'.

An X-ray b' impinging upon the channel 1' is parallel with the X-ray a that impinged upon the center channel 0 when the X-ray focal spot lay at a position designated as reference numeral 200. If the signal of the channel 1 is collected at this time, a signal of the channel 1 representing an X-ray parallel to the X-ray a can be obtained.

As the X-ray emitting/detecting apparatus rotates, a similar condition occurs for the other channels, and therefore, signals of all channels can be obtained as parallel beam X-rays by collecting the signals of the individual channels at individual times; and moreover, such signals can be obtained for a plurality of views with an angular step difference $\Delta\phi$.

Figure 12:
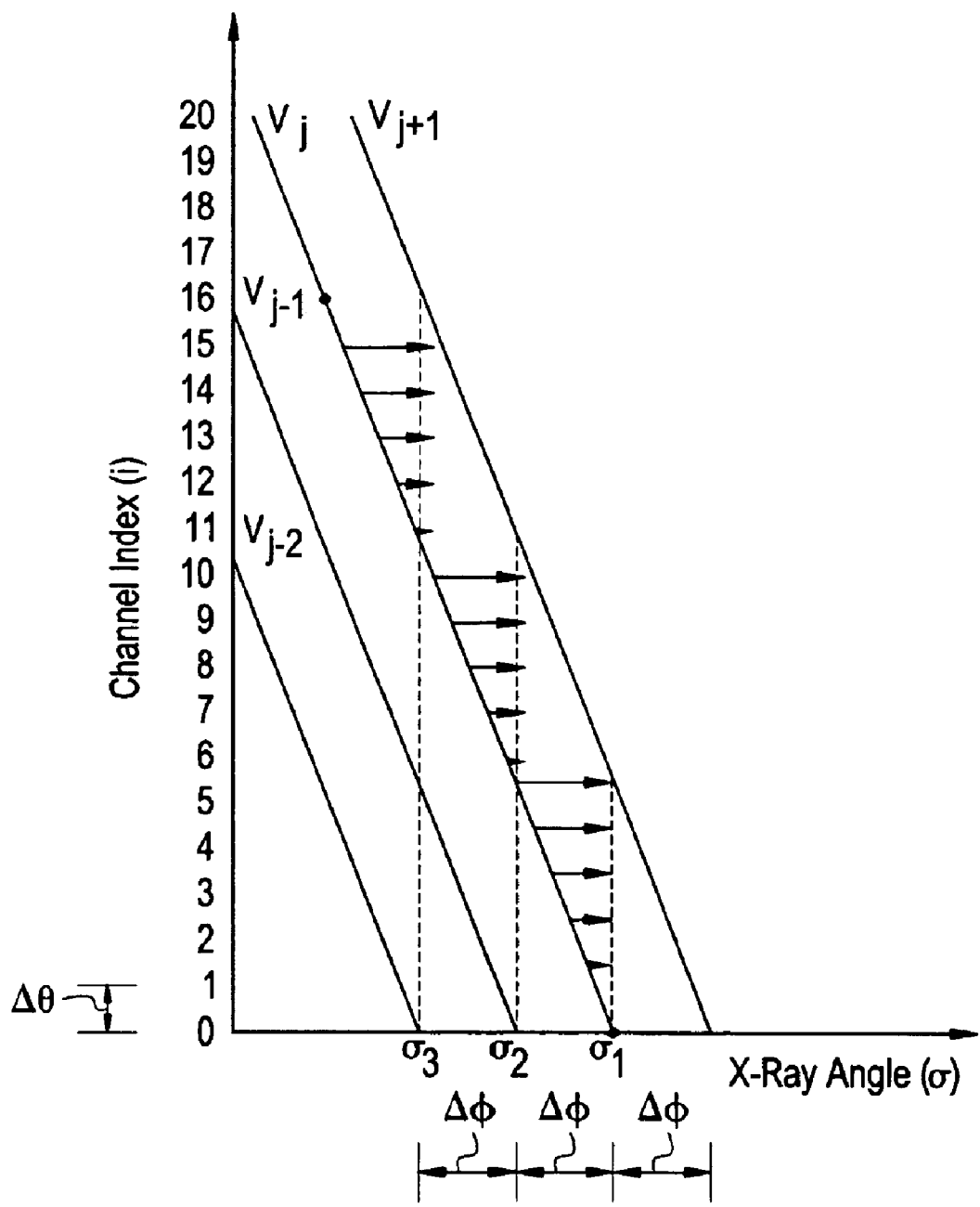
FIG. 12 shows transformation of fan beam data into parallel beam data.

FIG. 12 shows an example of times for transforming a fan beam into a parallel beam. FIG. 12 is a diagram representing X-ray angles versus channels, with the X-ray angle σ on the transverse axis and the channel index i on the vertical axis. Vj is a diagram line indicating fan beam X-rays at a view reference position Vj, and Vj+1 is a diagram line indicating fan beam X-rays at a view reference position Vj+1. The angular difference between Vj and Vj+1 is $\Delta\phi$. As the X-ray emitting/detecting apparatus rotates, the diagram line continuously translates from the view reference position Vj to view reference position Vj+1. The view reference position will be sometimes referred to simply as the view hereinbelow.

In the view Vj, the X-ray angle at the channel 0 is σ1. For the channel 1 and following channels, the X-ray angle is different by the angular step difference $\Delta\theta$ for each channel. The length of the arrow drawn from the diagram line Vj in parallel with the transverse axis for each channel represents the amount of movement of the diagram line up to the time at which a signal in the parallel beam X-rays is obtained for that channel.

For the channels 1–5, by collecting signals when the diagram line has been moved up to the tip positions of the arrows, signals in the parallel beam X-rays at the angle of σ1 can be obtained. The X-ray angle is the same as that of the channel 0 in the current view Vj. That is, X-ray signals in the parallel beam X-rays of the current view Vj are obtained.

For the channels 6–10, by collecting signals when the diagram line has been moved up to the tip positions of the arrows, signals in the parallel beam X-rays at the angle of σ2 can be obtained. The X-ray angle is the same as that of the channel 0 in the previous view Vj−1. That is, X-ray signals in the parallel beam X-rays of the previous view Vj−1 are obtained.

For the channels 11–15, by collecting signals when the diagram line has been moved up to the tip positions of the arrows, signals in the parallel beam X-rays at the angle of σ3 can be obtained. The X-ray angle is the same as that of the channel 0 in the second previous view Vj−2. That is, X-ray signals in the parallel beam X-rays of the second previous view Vj−2 are obtained.

For the channel 16 and following channels, the above process is repeated for every 16 channels. By conducting such signal collection for all views, X-ray signals in the parallel beam X-rays of all views are obtained.

Moreover, by simultaneously conducting such X-ray signal collection for all detector element rows, X-ray signals in the parallel beam X-rays of all views are obtained for all detector element rows.

Figure 13:
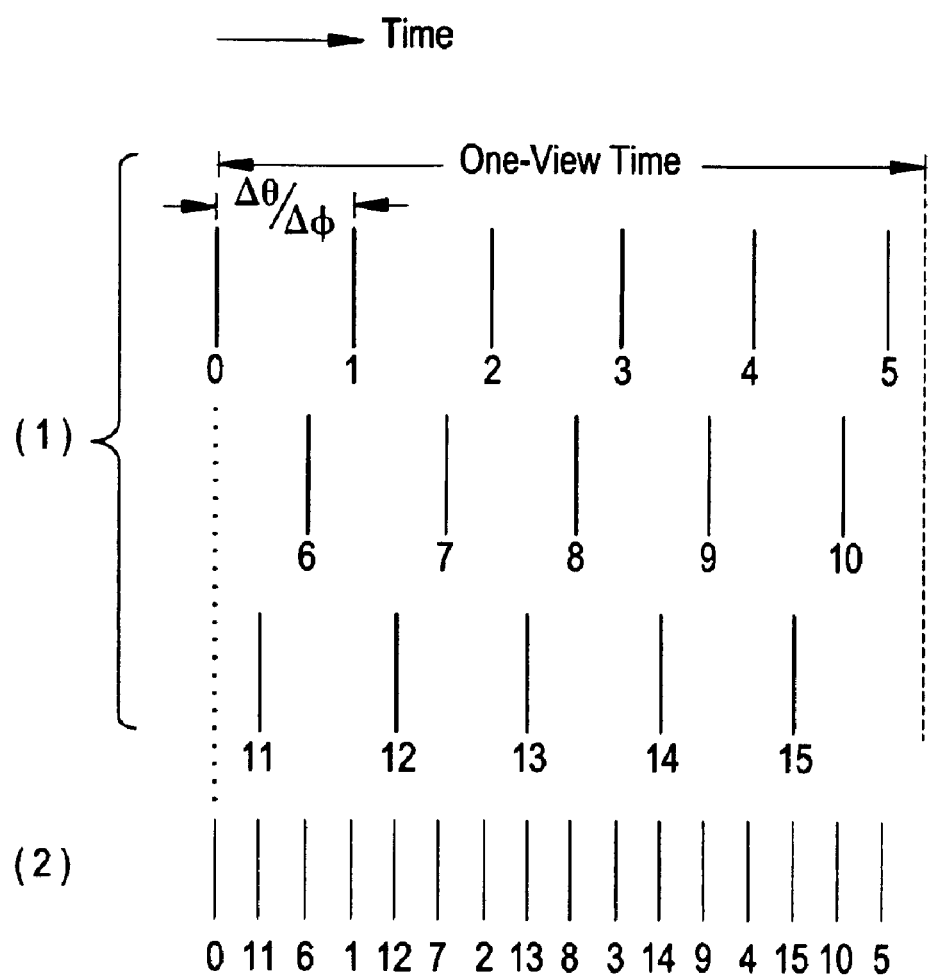
FIG. 13 shows times of signal collection.

FIG. 13 shows the times of signal collection for the channels 0–15 along a time axis. The times are shown by the time difference from the time of signal collection for the channel 0. As shown in FIG. 13(1), the time difference between the channels is $\Delta\theta/\Delta\phi$. It should be noted that the time difference is normalized by the time during which the diagram line translates by a view angular step difference of $\Delta\phi$. The time during which the diagram line translates by a view angular step difference of $\Delta\phi$ is equal to the time of $\Delta\phi$ rotation of the X-ray emitting/detecting apparatus. The time will be sometimes referred to as the one-view time hereinbelow.

The times of signal collection for the channels 0–15 are determined as those sequentially occurring at the time difference $\Delta\phi/\Delta\phi$, from which times the one-view time is subtracted after each one-view time has passed. Thus, a sequence of the times with reference to the channel 0 is 0, 11, 6, 1, 12, 7, 2, 13, 8, 3, 14, 9, 4, 15, 10, 5, as shown in FIG. 13(2). The time difference between these times is $1/16$. It should be noted that the value is normalized by the one-view time. The same applies to channels other than the channels 0–15 for every consecutive 16 channels.

Figure 14:
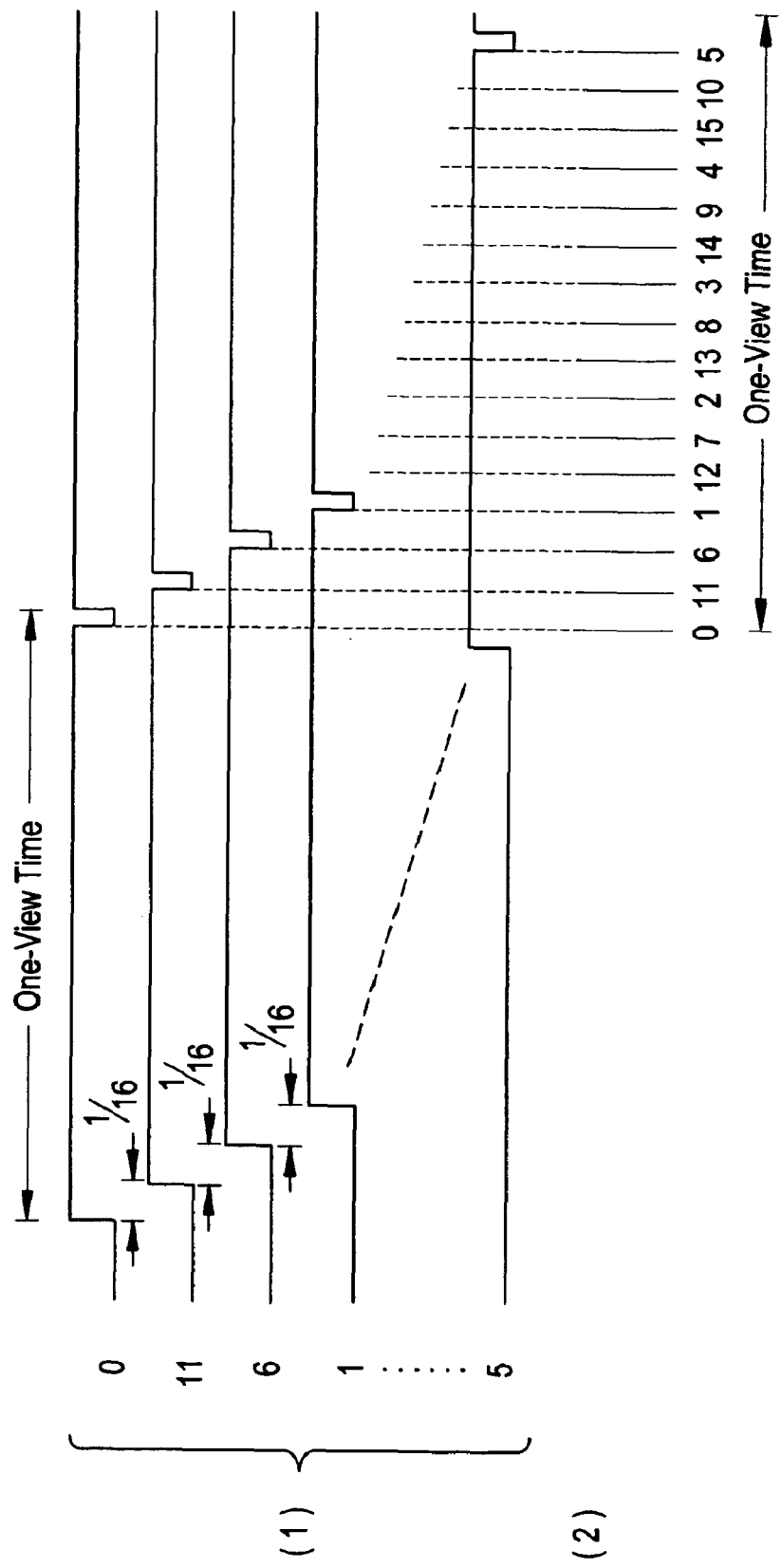
FIG. 14 shows times of measured signal integration.

The measured signal integrating section 904 executes integration at such times. A time chart thereof is shown in FIG. 14. As shown in FIG. 14(1), integration is executed on the sequence of the channels 0, 11, 6, 1, 12, 7, 2, 13, 8, 3, 14, 9, 4, 15, 10, 5 at a time difference of $1/16$.

The integration is repeatedly executed with a cycle of one-view time. At the end of each cycle, integral values are converted into digital data by an A/D (analog-to-digital) converter, and then reset. The A/D converter is incorporated in the measured signal integrating section 904.

Since the integral values are established in the sequence of the channels 0, 11, 6, 1, 12, 7, 2, 13, 8, 3, 14, 9, 4, 15, 10, 5 at a time difference of $1/16$, the times of the A/D conversion are in the same sequence. This is shown in FIG. 14(2). It is sufficient to provide one A/D converter unit for every 16 channels because the times do not overlap one another.

Figure 15:
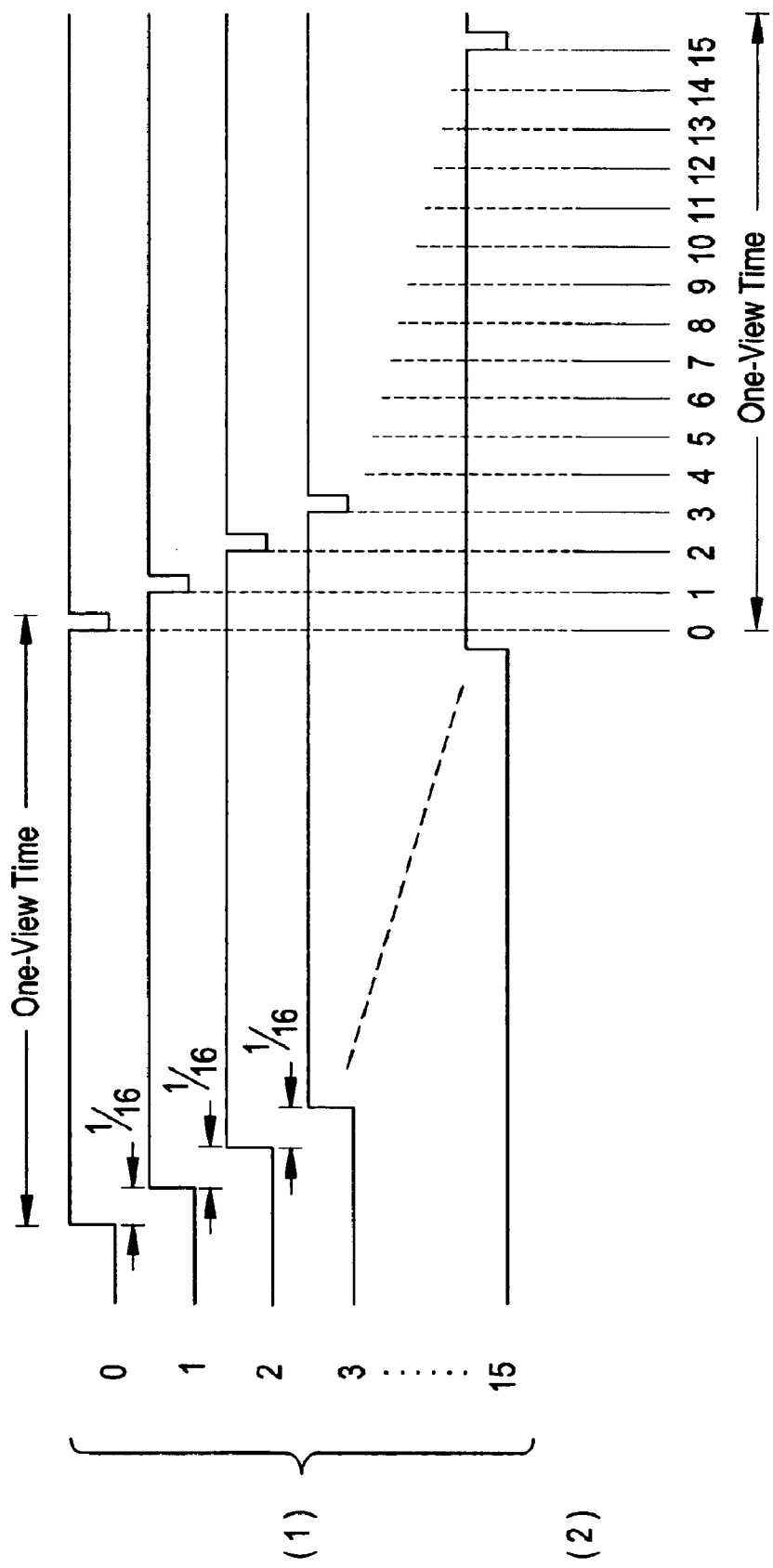
FIG. 15 shows times of reference signal integration.

Synchronously with such an operation of the measured signal integrating section 904, the reference signal integrating section 906 integrates signals of the reference channels 0–15. A time chart thereof is shown in FIG. 15. As shown in FIG. 15(1), the integration is executed in, for example, a sequence of channels 0, 1, 2, . . . , 15 at a time difference of ¹⁄₁₆. The sequence of the integration, however, is not limited thereto but may be an appropriate one.

The integration is repeatedly executed with a cycle of one-view time. At the end of each cycle, integral values are converted into digital data by an A/D converter, and then reset. The A/D converter is incorporated in the reference signal integrating section 906.

Since the integral values are established in the sequence of the reference channels 0, 1, 2, . . . , 15 at a time difference of ¹⁄₁₆, the times of the A/D conversion are in the same sequence. This is shown in FIG. 15(2). It is sufficient to provide one A/D converter unit for every 16 channels because the times do not overlap.

In general, when the number of signals input to the A/D converter that are sequentially processible within the one-view time is represented as n, and a number having no divisor in common with n is represented as p, Δθ and Δϕ can be determined so that $$\frac{\Delta\theta}{\Delta\phi} = \frac{p}{n}$$

is satisfied to conduct A/D conversion without overlap. The same applies to the A/D converter in the measured signal integrating section 904. Likewise, this applies not only to A/D conversion but also to other processing units that conduct sequential processing.

The times of integration of the reference channels 0, 1, 2, 3, . . . , 15 coincide with the times of integration of 16 measurement channels 0, 11, 6, 1, . . . , 5, respectively. Thus, reference signals at respective integration times for the measurement channels can be obtained.

Thus, integral values of signals detected by the reference channels 0, 1, 2, 3, . . . , 15 can be used as reference signals for integral values of signals detected by the measurement channel 0, 11, 6, 1, . . . , 5, respectively. Moreover, the integral values of signals detected by the reference channels 0, 1, 2, 3, . . . , 15 are also used as reference signals for integral values of signals detected by other measurement channels that are integrated at similar timing to that of the measurement channel 0, 11, 6, 1, . . . , 5.

Since the signals detected by the reference channels are continuously integrated at the same time as signals detected by the measurement channels in the one-view time as described above, reference signals with better S/N can be obtained than in the conventional technique that uses sums of values obtained by repeating integration/resetting at subdivided times of the one-view time.

The correcting section 910 corrects measured data from the measurement channels supplied from the measured signal integrating section 904 by reference data such as described above supplied from the reference signal integrating section 906. This correction removes the influence by a temporal change in X-ray intensity. The corrected data are input to the image reconstructing section 210. The image reconstructing section 210 reconstructs an image based on the input data. The reconstructed image has good quality because S/N of the reference data is good.

If reception of X-rays by the reference channels is hampered for some reason, the reference data becomes inaccurate and so does measured data corrected by the reference data, which may result in the quality of the reconstructed image being lowered. Accordingly, the correcting section 910 monitors the reference data, and conducts the correction by the reference data only if the reliability of the reference data is high or by alternative data if the reliability is low.

The reliability of the reference data is determined by the following equation:

$$1 - \varepsilon \le \left|\frac{R_{k(view)}}{R_{k(view-1)}}\right| \le 1 + \varepsilon,$$

where:
Rk(view): reference data of a current view at a reference channel k,
Rk(view-1): reference data of signals of a previous view at a reference channel k, and
ε: an allowance.

If Rk(view) does not satisfy the relationship, Rk(view)' given by the following equation is alternatively used as the reference data of the current view:

$$R'_{k(view)} = R_{k(view-1)} \cdot \frac{mA_{(view)}}{mA_{(view-1)}},$$

where:
mA(view): a tube current of the X-ray tube for the current view, and
mA(view-1): a tube current of the X-ray tube for the previous view.

Thus, influence from bad reference data can be avoided.

Figure 16:
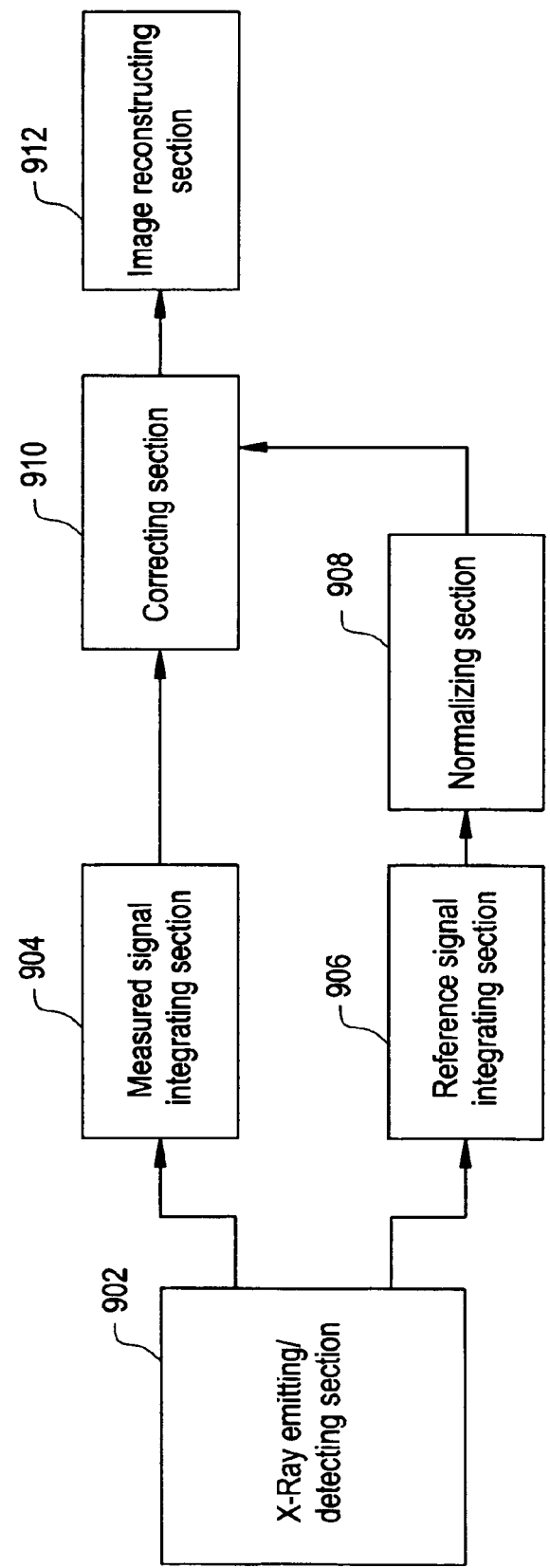
FIG. 16 is a functional block diagram of an apparatus in accordance with an embodiment of the present invention.

FIG. 16 shows a functional block diagram of the present apparatus. In FIG. 16, portions similar to those shown in FIG. 10 are designated as similar reference symbols, and explanation thereof will be omitted. The present apparatus has a normalizing section 908. The normalizing section 908 normalizes output data from the reference signal integrating section 906 and inputs the normalized signal to the correcting section 910. The normalizing section 908 is an embodiment of the normalizing means in the present invention.

When the fan beam X-rays 400 have an inhomogeneous intensity distribution in the beam thickness direction, reference data of the reference channels can be normalized to remove influence by the intensity distribution in the thickness direction. The normalizing section 908 conducts such normalization on the reference data.

Figure 17:
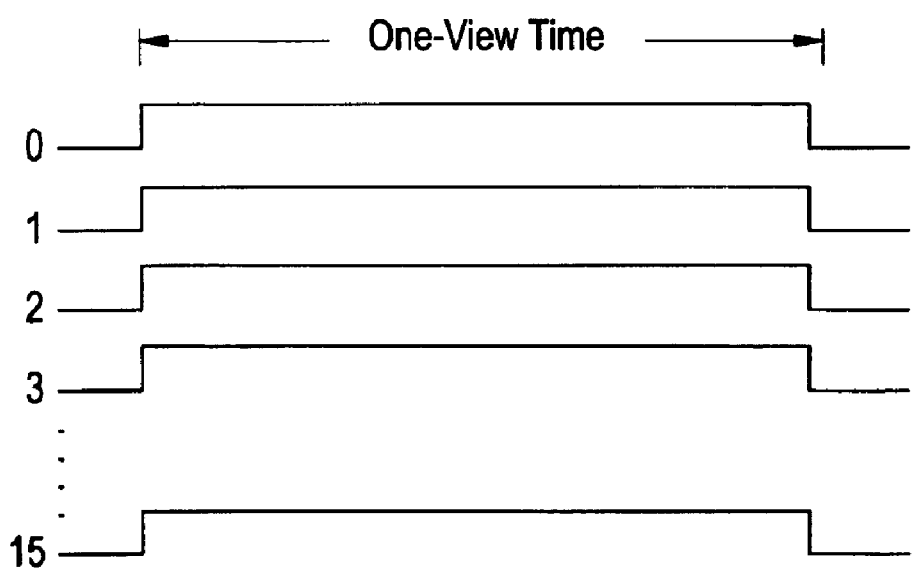
FIG. 17 shows times of baseline signal integration.

The normalization is achieved by dividing reference data Rk (k=0, 1, . . . , 15) for the reference channels by baseline data Ck for the reference channels. The baseline data Ck are obtained beforehand by integrating detected signals from the reference channels together at the same time over the one-view time, as shown in FIG. 17. Since the thus-obtained baseline data Ck incorporates therein an intensity distribution in the thickness direction, influence by the intensity distribution can be removed by dividing the reference data for the corresponding reference channels by those baseline data.

Although the present invention has been described with reference to the preferred embodiments hereinabove, several changes and substitutions may be made on these embodiments by those ordinarily skilled in the art to which the present invention pertains without departing from the scope of the present invention. Therefore, the technical scope of the present invention is intended to encompass not only the aforementioned embodiments but all embodiments pertaining to the appended claims.

What is claimed is:
1. An X-ray data collecting apparatus comprising:
an X-ray emitting/detecting device having an X-ray emitting apparatus including an X-ray tube for emitting a fan-shaped X-ray beam and an X-ray detection apparatus including a plurality of detector element rows in a thickness direction of said fan-shaped X-ray beam, in each of which rows a plurality of X-ray detector elements are arranged in an extent direction of said fan-shaped X-ray beam, said X-ray detection apparatus disposed to face said X-ray emitting apparatus interposing a subject, said X-ray emitting/detecting device rotating around said subject;

a first integrating device for periodically executing sequential integration on detected signals from a plurality of X-ray detector elements corresponding to measurement channels in said X-ray detection apparatus at a constant time difference over a constant time period longer than said time difference;

a second integrating device for periodically executing sequential integration detected signals from a plurality of X-ray detector elements corresponding to reference channels in said plurality of detector element rows in said X-ray detection apparatus at the same time difference as said constant time difference over the same time period as said constant time period; and a correcting device for correcting X-ray-dose signals integrated by said first integrating device by signals integrated by said second integrating device that are integrated at the same time as the signals integrated by said first integration device, respectively.

2. The X-ray data collecting apparatus of claim 1, wherein said X-ray detection apparatus is quarter-offset with respect to said X-ray emitting apparatus.

3. The X-ray data collecting apparatus of claim 1, wherein said plurality of X-ray detector elements are arranged symmetrically with respect to a center of the detector element rows.

4. The X-ray data collecting apparatus of claim 1, wherein said time difference is one such that X-ray beams impinging upon a plurality of measurement channels are parallel.

5. The X-ray data collecting apparatus of claim 1, wherein when a difference in time of integration between adjacent channels in said detector element row is represented as $\Delta\theta/\Delta\phi$ (normalized by $\Delta\phi$), the number of channels handled per unit by processing device for sequentially processing output signals from at least one of said first integrating device and said second integrating device is represented by n, and integer having no divisor in common with n is represented as p, said time difference enables these variables to satisfy:

$$\frac{\Delta\theta}{\Delta\phi} = \frac{p}{n},$$

where:
$\Delta\theta$: an angular step difference for measurement channels, and
$\Delta\phi$: an angular step difference for views.

6. The X-ray data collecting apparatus of claim 1, further comprising:
a normalizing device for normalizing output signals from said second integrating device.

7. The X-ray data collecting apparatus of claim 6, wherein said normalizing device determines a plurality of integral values beforehand by integrating detected signals from all reference channels at the same time over said constant time period, and normalizes said output signals from said second integrating device for the reference channels by said plurality of integral values of the same reference channels, respectively.

8. The X-ray data collecting apparatus of claim 1, wherein if $$1 - \varepsilon \le \left|\frac{R_{k(view)}}{R_{k(view-1)}}\right| \le 1 + \varepsilon,$$

where:
Rk(view): an integral value of signals of a current view at a reference channel k over said constant time period,
Rk(view-1): an integral value of signals of a previous view at a reference channel k over said constant time period, and
ϵ: an allowance,
does not hold, said correcting device conducts the correction using, in place of Rk(view), $$R'_{k(view)} = R_{k(view-1)} \cdot \frac{mA_{(view)}}{mA_{(view-1)}},$$

where:
mA(view): a tube current of the X-ray tube for the current view, and
mA(view-1): a tube current of the X-ray tube for the previous view.

9. An X-ray CT apparatus comprising:
an X-ray emitting/detecting device having an X-ray emitting apparatus including an X-ray tube for emitting a fan-shaped X-ray beam and an X-ray detection apparatus including a plurality of detector element rows in a thickness direction of said fan-shaped X-ray beam, in each of which rows a plurality of X-ray detector elements are arranged in an extent direction of said fan-shaped X-ray beam, said X-ray detection apparatus disposed to face said X-ray emitting apparatus interposing a subject, said X-ray emitting/detecting device rotating around said subject;

a first integrating device for periodically executing sequential integration on detected signals from a plurality of X-ray detector elements corresponding to measurement channels in said X-ray detection apparatus at a constant time difference over a constant time period longer than said time difference;

a second integrating device for periodically executing sequential integration on detected signals from a plurality of X-ray detector elements corresponding to reference channels in said plurality of detector element rows in said X-ray detection apparatus at the same time difference as said constant time difference over the same time period as said constant time period;

a correcting device for correcting X-ray-dose signals integrated by said first integrating device by signals integrated by said second integrating device that are integrated at the same time as the signals integrated by said first integration device, respectively; and an image reconstructing device for producing an image based on said corrected signals.

10. The X-ray CT apparatus of claim 9, wherein said X-ray detection apparatus is quarter-offset with respect to said X-ray emitting apparatus.

11. The X-ray CT apparatus of claim 9, wherein said plurality of X-ray detector elements are arranged symmetrically with respect to a center of the detector element rows.

12. The X-ray CT apparatus of claim 9, wherein said time difference is one such that X-ray beams impinging upon a plurality of measurement channels are parallel.

13. The X-ray CT apparatus of claim 9, wherein when a difference in time of integration between adjacent channels in said detector element row is represented as Δθ/Δφ (normalized by Δφ), the number of channels handled per unit by processing device for sequentially processing output signals from at least one of said first integrating device and said second integrating device is represented by n, and an integer having no divisor in common with n is represented as p, said time difference enables these variables to satisfy:

$$\frac{\Delta\theta}{\Delta\phi} = \frac{p}{n},$$

where:
Δθ: an angular step difference for measurement channels, and
Δφ: an angular step difference for views.

14. The X-ray CT apparatus of claim 9, further comprising:
a normalizing device for normalizing output signals from said second integrating device.

15. The X-ray CT apparatus of claim 14, wherein said normalizing device determines a plurality of integral values beforehand by integrating detected signals from all reference channels at the same time over said constant time period, an normalizes said output signals from said second integrating device for the reference channels is by said plurality of integral values of the same reference channels, respectively.

16. The X-ray CT apparatus of claim 9, wherein if $$1 - \varepsilon \le \left|\frac{R_{k(view)}}{R_{k(view-1)}}\right| \le 1 + \varepsilon,$$

where:
Rk(view): an integral value of signals of a current view at a reference channel k over said constant time period,
Rk(view-1): an integral value of signals of a previous view at a reference channel k over said constant time period, and
ε: an allowance, does not hold, said correcting device conducts the correction using, in place of Rk(view), $$R'_{k(view)} = R_{k(view-1)} \cdot \frac{mA_{(view)}}{mA_{(view-1)}},$$

where:
mA(view): a tube current of the X-ray tube for the current view, and
mA(view-1): a tube current of the X-ray tube for the previous view.

* * * * *

UNITED STATES PATENT AND TRADEMARK OFFICE
CERTIFICATE OF CORRECTION

PATENT NO. : 6,937,697 B2
APPLICATION NO. : 10/738053
DATED : August 30, 2005
INVENTOR(S) : Nishide et al.

It is certified that error appears in the above-identified patent and that said Letters Patent is hereby corrected as shown below:

In Claim 5, column 13, line 45, between "and" and "integer" insert -- an --.
In Claim 15, column 15, line 25, delete "period, an" and insert therefor -- period, and --.
In Claim 15, column 15, line 27, delete "channels is by" and insert thereof -- channels by --.

Signed and Sealed this

Sixth Day of November, 2007

JON W. DUDAS
*Director of the United States Patent and Trademark Office*